(12) United States Patent
Zalevsky et al.

(10) Patent No.: US 9,500,875 B2
(45) Date of Patent: *Nov. 22, 2016

(54) IMAGING WITH EXTENDED DEPTH OF FOCUS FOR USE WITH POLYCROMATIC LIGHT

(71) Applicant: Brien Holden Vision Institute, Kensington, New South Wales (AU)

(72) Inventors: Zeev Zalevsky, Rosh HaAyin (IL); Alex Zlotnik, Ashdod (IL); Shai Ben-Yaish, Petach Tiqva (IL); Ofer Limon, Kfar-Saba (IL); Ido Raveh, Neve Yarak (IL)

(73) Assignee: Brien Holden Vision Institute, Kensington, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,569

(22) Filed: Jan. 7, 2015

(65) Prior Publication Data

US 2015/0198819 A1 Jul. 16, 2015

Related U.S. Application Data

(63) Continuation of application No. 13/578,176, filed as application No. PCT/IL2011/000142 on Feb. 9, 2011, now Pat. No. 8,955,968.

(60) Provisional application No. 61/302,588, filed on Feb. 9, 2010.

(51) Int. Cl.
*G02C 7/04* (2006.01)
*G02B 27/00* (2006.01)
(Continued)

(52) U.S. Cl.
CPC ............. *G02B 27/4205* (2013.01); *A61F 2/16* (2013.01); *A61F 2/1648* (2013.01); *G02B 5/18* (2013.01);
(Continued)

(58) Field of Classification Search
CPC ...... G02B 5/18; G02B 5/1528; G02B 5/1842; G02B 27/0075; G02B 27/00; G02C 7/02; G02C 7/022; G02C 7/04
USPC ............ 359/238, 738, 739, 740; 351/159.49, 351/159.59, 159.6, 159.65; 623/6.17
See application file for complete search history.

(56) References Cited

U.S. PATENT DOCUMENTS 3,549,240 A 12/1970 Sawatari
4,736,734 A 4/1988 Matsuura
(Continued)

FOREIGN PATENT DOCUMENTS

CN 101510012 8/2009
EP 0369561 5/1990
(Continued)

OTHER PUBLICATIONS

Hecht, Eugene: "Optik", Addison-Wesley Publishing Company, Bonn, Munchen, pp. 441-445, Dec. 31, 1989.
(Continued)

*Primary Examiner* — Darryl J Collins
(74) *Attorney, Agent, or Firm* — Jones Day

(57) ABSTRACT

An imaging lens unit is presented, comprising an imaging lens having a lens region defining an effective aperture, and a phase coder. The phase coder may be incorporated with or located close to the lens region. The phase coder defines a surface relief along the lens region formed by at least three phase patterns extending along the lens region. Each of the phase patterns differently affecting light components of one of at least three different wavelength ranges while substantially not affecting propagation of light components of other of said at least three wavelength ranges. The surface relief affects light propagation through the lens region to extend a depth of focus for at least one of said at least three wavelength ranges.

19 Claims, 2 Drawing Sheets

(51) Int. Cl.
*A61F 2/16* (2006.01)
*G02B 27/42* (2006.01)
*G02B 5/18* (2006.01)
*G02C 7/02* (2006.01)
*G02C 7/06* (2006.01)

(52) U.S. Cl.
CPC ........... *G02B 5/1828* (2013.01); *G02B 5/1895* (2013.01); *G02B 27/0025* (2013.01); *G02B 27/0037* (2013.01); *G02B 27/0075* (2013.01); *G02B 27/4211* (2013.01); *G02C 7/022* (2013.01); *G02C 7/04* (2013.01); *G02C 7/049* (2013.01); *A61F 2/1613* (2013.01); *G02C 7/06* (2013.01); *G02C 2202/22* (2013.01); *Y10S 977/902* (2013.01); *Y10S 977/932* (2013.01)

(56) References Cited

U.S. PATENT DOCUMENTS

| | | | |
|---|---|---|---|
| 4,923,296 | A | 5/1990 | Erickson |
| 4,955,904 | A | 9/1990 | Atebara |
| 5,117,306 | A | 5/1992 | Cohen |
| 5,158,572 | A | 10/1992 | Nielsen |
| 5,172,143 | A | 12/1992 | Baude |
| 5,198,844 | A | 3/1993 | Roffman |
| 5,225,858 | A | 7/1993 | Portney |
| 5,245,367 | A | 9/1993 | Miller |
| 5,260,727 | A | 11/1993 | Oksman |
| 5,299,062 | A | 3/1994 | Ogata |
| 5,302,477 | A | 4/1994 | Dao |
| 5,482,801 | A | 1/1996 | Smith |
| 5,543,966 | A | 8/1996 | Meyers |
| 5,662,706 | A | 9/1997 | Legerton |
| 5,674,282 | A | 10/1997 | Cumming |
| 5,682,223 | A | 10/1997 | Menezes |
| 5,715,031 | A | 2/1998 | Roffman |
| 5,748,371 | A | 5/1998 | Cathey |
| 5,757,458 | A | 5/1998 | Miller |
| 5,768,031 | A | 6/1998 | Yang |
| 5,788,883 | A | 8/1998 | Srivastava |
| 5,822,091 | A | 10/1998 | Baker |
| 5,864,379 | A | 1/1999 | Dunn |
| 5,905,561 | A | 5/1999 | Lee |
| 5,965,330 | A | 10/1999 | Evans |
| 5,980,040 | A | 11/1999 | Xu |
| 6,024,447 | A | 2/2000 | Portney |
| 6,069,738 | A | 5/2000 | Cathey, Jr. |
| 6,097,856 | A | 8/2000 | Hammond, Jr. |
| 6,172,957 | B1 | 1/2001 | Ogasawara |
| 6,451,056 | B1 | 9/2002 | Cumming |
| 6,474,814 | B1 | 11/2002 | Griffin |
| 6,488,708 | B2 | 12/2002 | Sarfarazi |
| 6,527,389 | B2 | 3/2003 | Portney |
| 6,533,416 | B1 | 3/2003 | Fermigier |
| 6,536,898 | B1 | 3/2003 | Cathey, Jr. |
| 6,537,317 | B1 | 3/2003 | Steinert |
| 6,554,424 | B1 | 4/2003 | Miller |
| 6,554,859 | B1 | 4/2003 | Lang |
| 6,576,012 | B2 | 6/2003 | Lang |
| 6,661,816 | B2 | 12/2003 | Delfyett |
| 6,685,315 | B1 | 2/2004 | De Carle |
| 7,025,454 | B2 | 4/2006 | Cathey, Jr. |
| 7,061,693 | B2 | 6/2006 | Zalevsky |
| 7,101,436 | B2 | 9/2006 | Taniguchi |
| 7,224,540 | B2 | 5/2007 | Olmstead |
| 7,365,917 | B2 | 4/2008 | Zalevsky |
| 7,411,743 | B2 | 8/2008 | Sugi |
| 7,569,312 | B2 | 8/2009 | Misaka |
| 7,646,549 | B2 | 1/2010 | Zalevsky |
| 7,859,769 | B2 | 12/2010 | Zalevsky |
| 8,169,716 | B2 | 5/2012 | Zalevsky |
| 2003/0142268 | A1 | 7/2003 | Miller |
| 2003/0197906 | A1 | 10/2003 | Furuta |
| 2004/0114102 | A1 | 6/2004 | Miller |
| 2004/0114103 | A1 | 6/2004 | Miller |
| 2004/0145808 | A1 | 7/2004 | Cathey, Jr. |
| 2004/0230299 | A1 | 11/2004 | Simpson |
| 2006/0082882 | A1 | 4/2006 | Wang |
| 2006/0176572 | A1 | 8/2006 | Fiala |
| 2008/0198482 | A1 | 8/2008 | Zalevsky |
| 2009/0074239 | A1 | 3/2009 | Zalevsky |
| 2009/0088840 | A1 | 4/2009 | Simpson |
| 2009/0112314 | A1 | 4/2009 | Server |
| 2009/0116096 | A1 | 5/2009 | Zalevsky |
| 2009/0147378 | A1 | 6/2009 | Zalevsky |
| 2009/0187242 | A1 | 7/2009 | Weeber |
| 2009/0279189 | A1 | 11/2009 | Getman |
| 2009/0303432 | A1 | 12/2009 | Suzuki |
| 2010/0075114 | A1 | 3/2010 | Kurihara |
| 2010/0118419 | A1 | 5/2010 | Cho |
| 2010/0149510 | A1 | 6/2010 | Zaczek |
| 2011/0082541 | A1 | 4/2011 | Zalevsky |

FOREIGN PATENT DOCUMENTS

| | | |
|---|---|---|
| JP | 2137815 | 5/1990 |
| WO | 9957599 | 11/1999 |
| WO | 200135880 | 5/2001 |
| WO | 2003012528 | 2/2003 |
| WO | 03032825 | 4/2003 |
| WO | 03052465 | 6/2003 |
| WO | 03052492 | 6/2003 |
| WO | 03076984 | 9/2003 |
| WO | 2004113994 | 12/2004 |
| WO | 2007141788 | 12/2007 |
| WO | 2009115932 | 9/2009 |
| WO | 2009140080 | 11/2009 |
| WO | 2010009254 | 1/2010 |

OTHER PUBLICATIONS

Bradburn Setal: "Realizations of focus invariance in optical-digital systems with wave-front coding", Applied Optics, OSA, Optical Society of America, US, vol. 36, No. 35, Dec. 10, 1997, pp. 9157-9166.

L. A. Carvalho. "A simple mathematical model for simulation of the human optical system based on in vivo corneal data." Revista Brasileira de Engenharia Biomedica, 19, 29-37 (2003).

Fitzgerrell A R et al: "Defocus transfer function for circularly symmetric pupils", Applied Optics OPT. Soc. America USA, val. 36, No. 23, Aug. 10, 1997, pp. 5796-5804.

Varamit C et al: "Imaging properies of deocused paritioned pupils" Jounal of the Optical Sociey of America A (Optics and Image Science) USA, val. 2, No. 6, Jun. 1985, pp. 799-802.

H. Wang and F. Gan, "High focal depth with pure-phase apodizer", Applied Optics, vol. 40, No. 31, pp. 5658-5662, (Nov. 1, 2001).

Kahn, A. (2007). Visual adaptation: physiology, mechanisms, and functional benefits. J Neurophysiol, 97 (5), 3155-3164.

Webster, M.A., Georgeson, M.A., & Webster, S.M. (2002). Neural adjustments to image blur. Nat Neurosci, 5 (9), 839-840.—abstract only.

Pesudovs, K., & Brennan, N A (1993). Decreased uncorrected vision after a period of distance fixation with spectacle wear. Optom Vis Sci, 70 (7), 528-531.—abstract only.

Yehezkel 0., Belkin M., Sagi D. & Polat U. (2005). Adaptation to astigmatic lens: effects on lateral interactions Visual Sciences Society Annual Meeting.—abstract only.

Webster, M., Sawides, L. Ravikumar, S., Thibos, L. Bradley, A., & Marcos, S. (2009). Adapting to astigmatism. Journal of Vision, 9(8):986, 986a.—abstract only.

Forrest, E.B. (1984). Eye Scan Therapy For Astigmatism. Journal of the American Optometric Association, 55(12): 894-901—abstract only.

T. Callina and T. P. Reynolds. "Traditional methods for the treatment of presbyopia: spectacles, contact lenses, bifocal contact lenses," Ophthalmology Clinics of North America, 19(1), 25-33 (2006).—abstract only.

(56) References Cited

OTHER PUBLICATIONS

C. W. Fowler and E. S. Pateras, "A gradient-index ophthalmic lens based on Wood's convex pseudo-lens," Ophthalmic and Physiological Optics, 10(3), 262-70 (1990).—abstract only.

C. M. Sullivan and C. W. Fowler, "Progressive addition and variable focus lenses: a review," Ophthalmic and Physiological Optics, 8(4), 402-14 (1988).—abstract only.

Di Feng, Pan Ou, Li-Shuang Feng, Shu-Ling Hu, and Chun-Xi Zhang, "Binary sub-wavelength diffractive lenses with long focal depth and high transverse resolution," Opt. Express 16, 20968-20973 (2008).

Joseph N. Mail, Axel Scherer, Oliver Dial, Dennis W. Prather, and Xiang Gao, "Diffractive lens fabricated with binary features less than 60 nm," Opt. Lett. 25, 381-383 (2000).

Michael W. Farn, "Binary gratings with increased efficiency," Appl. Opt. 31, 4453-4458 (1992).

Yehezkel, 0., Sagi, D., Sterkin, A., Belkin, M., & Polat, U. Learning to adapt: Dynamics of readaptation to distortions. Vision Research, 50 (2010), 1550-1558.

Petit, R., and G. Bouchitre, "Replacement of a very fine grating by a stratified layer: homogenization techniques and the ultiplescale method," SPIE Proceedings Application and Theory of Periodic Structures, Diffraction Gratings, and Moir'e Phenomena 431, vol. 815, ed. J. Lerner, 1987.

Zalevsky et al: "All-optical axial super resolving imaging using a low-frequency binary-phase mask" Optics Express, OSA (Optical Society of America), Washington DC US, val. 14, No. 7, Apr. 3, 2006, pp. 2631-2643.

Sales T R M etal: "Diffractive supperresolution elements", Journal of the optical society of America, val. 14, No. 7, Jul. 1997, pp. 1637-1646.

De Juana D M et al: "Focusing properties of annular binary phase filters", Optics Communications, North-Holland Publishing Co., Amsterdam, NL, val. 229, No. 1-6, Jan. 2, 2004, pp. 71-77.

IMAGING WITH EXTENDED DEPTH OF FOCUS FOR USE WITH POLYCROMATIC LIGHT

CROSS REFERENCE TO RELATED APPLICATION

This application a continuation of U.S. application Ser. No. 13/578,176, filed Oct. 23, 2012, which is the National Phase application of International Application No. PCT/IL2011/000142, filed Feb. 9, 2011, which designates the United States and was published in English, which claims priority to U.S. Provisional Application No. 61/302,588, filed Feb. 9, 2010. These applications, in their entirety, are incorporated herein by reference.

FIELD OF THE INVENTION

This invention relates to imaging with extended depth of focus, and an imaging lens unit configured accordingly, using polychromatic illumination.

BACKGROUND OF THE INVENTION

Extending the depth of focus of an imaging system is required for various applications, including medical application, such as ophthalmic applications. Various techniques have been developed to extend the depth of focus of an imaging system.

For example, the earlier technique developed by the inventors of the present application provides an extended depth of focus of an imaging lens unit by applying a phase coding to the effective aperture of the imaging lens. The features of this technique are described in the following patents and published patent applications: U.S. Pat. No. 7,365,917; U.S. Pat. No. 7,061,693; US 2009/074239; US 2009/116096; U.S. Pat. No. 7,646,549, all assigned to the assignee of the present application. Some other techniques for extending depth of focus for imaging and other optical applications are described for example in the following patents: U.S. Pat. No. 6,554,424, U.S. Pat. No. 6,097,856 and U.S. Pat. No. 6,069,738.

Yet another technique is disclosed for example, U.S. Pat. No. 7,224,540, which describes an imaging system that has a wavelength dependent focal shift caused by longitudinal chromatic aberration in a lens assembly that provides extended depth of field imaging due to focal shift and increased resolution due to reduced lens system magnification. In use, multiple wavelengths of quasi-monochromatic illumination, from different wavelength LEDs or the like, illuminate the target, either sequentially, or in parallel in conjunction with an imager with wavelength selective (colored) filters. Images are captured with different wavelengths of illumination that have different focus positions, either sequentially or by processing the color planes of a color imager separately. Extended depth of field, plus high resolution is achieved. Additionally, information about the range to the target can be determined by analyzing the degree of focus of the various colored images.

GENERAL DESCRIPTION

There is a need in the art for a novel imaging lens unit operable with polychromatic illumination and configured to extend the depth of focus while maintaining high contrast imaging.

In order to enable imaging with the extended depth of focus the present invention provides a novel all-optical technique capable of obtaining an extended depth with desirably high-contrast by intentionally introducing appropriate chromatic aberrations in the imaging process. To this end, the invention provides a lens unit configured for imaging different light components of different wavelength ranges onto regions properly displaced with respect to one another along the optical axis, providing together an extended focal region, while an original lens used in the lens unit may be configured with chromatic aberration correction.

In imaging optics, chromatic aberration is a type of distortion that occurs when a lens focuses different wavelengths (different colors) of light onto different spots in the image plane or onto different planes. This distortion is caused by different refraction effects of lens onto different wavelength components of light propagating through the lens (i.e. different refractive indices of the lens matter for different wavelength components of light), thus differently affecting the propagation of light emerging from the lens.

Imaging systems are usually designed for use with a polychromatic wavelength range. To do so, an imaging system has to consider the changes of the refractive index over different wavelengths. This refractive index changes provide different optical powers of a lens for different wavelengths of light and therefore create chromatic aberrations. For example, in a fused silica, crown glass or BK7 lens with optical power of 1 diopter at green illumination the focal length for red or blue illumination will differ by 1-2 centimeters, if nothing is done to correct chromatic aberrations. An imaging lens may be treated to prevent chromatic aberrations by addition of a second lens to form a lens unit with reduced aberrations, or by providing an appropriate coating on the lens' surface.

The technique of the present invention utilizes phase coder extending along a lens region of an imaging lens (the imaging lens by itself may or may not be treated to prevent chromatic aberrations). The phase coder defines a patterned structure formed by at least three phase affecting patterns each configured to affect the phase of light components of one of at least three spectral ranges while substantially not affecting phase of light components of other spectral ranges. Additionally, one or more of these phase patterns may be configured to provide focus shift for the corresponding spectral, range(s).

At least one of the at least three phase patterns is configured to provide imaging with extended depth of focus for the corresponding spectral range. For example, any of such at least three phase patterns may be configured as described in U.S. Pat. No. 7,365,917 assigned to the assignee of the present application, or may be formed by optical masks and phase patterning as described in U.S. Pat. No. 6,554,424, 6,097,856 or 6,069,738, all being incorporated herein by reference.

The phase pattern may be formed by a ring-like or grid-like arrangement of phase affecting regions, and is preferably configured to be non-diffractive.

Providing an imaging lens unit with capability to affect spectral ranges by different phase patterns respectively enables generation of a through focus MTF appropriately tailored for providing an extended depth of focus while maintaining high contrast imaging.

Preferably, the tailored through focus MTF is configured to provide proper axial displacement of the focal points for different wavelength ranges (chromatic channels) to provide imaging quality in which the spatial information of one channel is in focus and the information in the other channels is relatively blurred. The proper axial displacement may provide for large extension of the depth of focus and extension of visibility. For every axial distance, a different combination of one or more in focus chromatic channels and one or more two defocused channels may be obtained.

The imaging lens unit of the present invention is specifically useful for various ophthalmic applications in which the brain adaptation process of a user can sharpen the information of the two defocused channels. Such adaptation process can be done since the visual spatial information received by the brain is based on a focused chromatic channel. The imaging lens unit of the present invention may be used as spectacles lens, or for use in other ophthalmic applications, as intraocular lens, intracorneal lens or a contact lens.

The different phase patterns configured to affect light components of specific chromatic channels respectively while not affecting other light components may be such "color selective" by utilizing the periodicity of electromagnetic wave cycles.

Considering a phase pattern designed to affect light of a specific wavelength range, said phase pattern is designed such that it affects light components of other wavelength ranges by addition of an integer number of cycles ($2\pi N$ phase difference) while affecting the specific desired wavelength range by addition of a non-integer phase difference.

Thus, according to one broad aspect of the invention, there is provided an imaging lens unit comprising an imaging lens having a lens region defining an effective aperture, and a phase coder, said phase coder being incorporated with or located close to said lens region, said phase coder defining a surface relief along the lens region formed by at least three phase patterns extending along said lens region, each phase pattern differently affecting light components of one of at least three different wavelength ranges while substantially not affecting propagation of light components of other of said at least three wavelength ranges, said surface relief affecting light propagation through the lens region to extend a depth of focus for at least one of said at least three wavelength ranges.

Generally, the phase coder comprises a mask associated with a surface of the imaging lens within said lens region, where said mask has one of the following configurations: (i) is integral with the lens region, in which case the surface relief is formed on at least one of the surfaces of the lens within said lens region; and (ii) is attached to the lens region, (iii) being spaced-apart from the lens region along an optical axis of the imaging lens.

The surface relief is a pattern formed by superposition of said at least three patterns. The surface relief pattern has features arranged along said lens region and having predetermined dimensions along said lens region and along an optical axis of the imaging lens. The surface relief may be configured to correspond to a predetermined height profile along the lens region, such that when polychromatic light passes through said lens region, a depth of focus for at least one of said at least three wavelength ranges in said light is extended, e.g. depths of focus for at least three wavelength ranges in said light are extended.

Preferably, said at least three wavelength ranges correspond to those of primary colors.

The phase pattern may be formed by at least one closed-loop zone of a thickness different from that of its surrounding within the lens region. Such a closed-loop zone may have a ring-like geometry, or a polygonal geometry. The phase pattern may be formed by at least two elongated spaced-apart zones of a thickness different from that within a space between the zones.

According to another broad aspect of the invention, there is provided an imaging lens unit comprising an imaging lens having a lens region and an optically transparent phase mask designed to provide at least three phase variation patterns to light components of at least three chromatic channels respectively, the optically transparent mask having a height profile $\delta d$ with respect to the lens region thereby providing said at least three phase variation patterns, the height profile $\delta d$ being configured to satisfy the following condition:

$$\delta d(x) = \frac{\lambda_R}{2\pi(n-1)}(2\pi N_R(x) + \varphi_d^{(R)}(x))$$

$$= \frac{\lambda_G}{2\pi(n-1)}(2\pi N_G(x) + \varphi_d^{(G)}(x))$$

$$= \frac{\lambda_B}{2\pi(n-1)}(2\pi N_B(x) + \varphi_d^{(B)}(x))$$

wherein, $\lambda_R$, $\lambda_G$ and $\lambda_B$ are wavelengths defining at least three chromatic channels, $\varphi_d^{(R)}(x)$, $\varphi_d^{(G)}(x)$, $\varphi_d^{(B)}(x)$ are said phase variation patterns, a is a refractive index of a material of said optically transparent mask, $N_R$, $N_G$ and $N_B$ are integer numbers, and x is a position vector along said lens region;

at least one of said phase variation patterns being configured to provide imaging with extended depth of focus for the respective chromatic channel.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
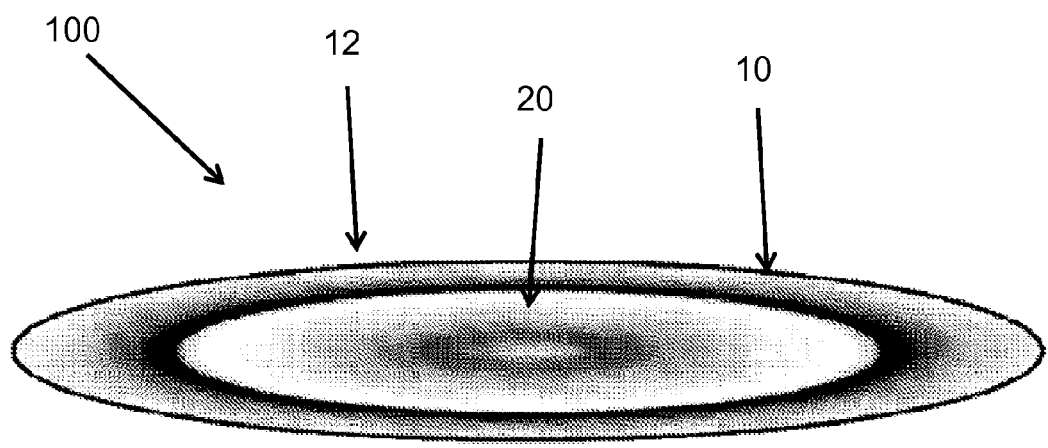
FIG. 1 schematically illustrates and example of imaging lens unit according to the invention.

Reference is made to FIG. 1 illustrating an example of an imaging lens unit 100. The imaging lens unit includes an imaging lens 10 having a lens region 12 and a phase coder 20 on top of the imaging lens. The imaging lens unit may also include other lenses, apertures, a detector or other optical element not specifically shown in this example.

The phase coder 20 is extending along the lens region 12 and configured to provide phase encoding to light passing through the imaging lens 10 of the imaging lens unit 100. The phase encoding may be integral with the imaging lens 10, or it may be a phase mask integral with the lens 10, attached to the lens or located close thereto. The phase coder defines at least three phase patterns, each designed to affect light components of a specific wavelength range, to provide extended depth of focus to the lens system for the specific wavelength range while not affecting light components of other wavelength ranges. It should e noted that the imaging lens 10 may be treated to prevent chromatic aberrations or not.

Figure 2:
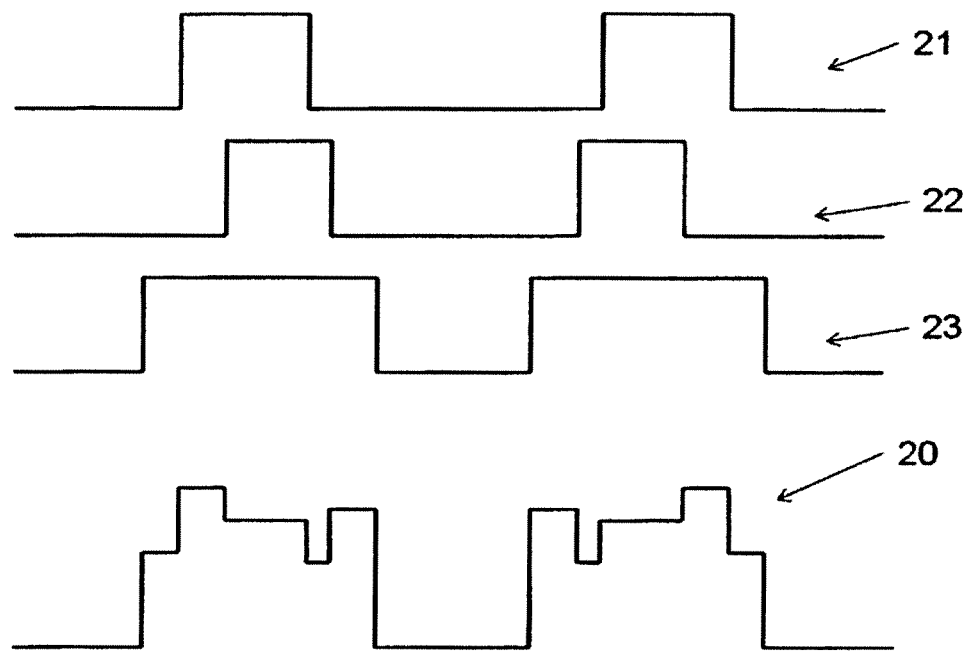
FIG. 2 exemplifies the phase coder suitable to be used in the imaging lens unit of the present invention.

Reference is made to FIG. 2 showing a phase coder 20 presenting a so-called "combine" phase affecting pattern which is a superposition of three phase affecting patterns 21, 22 and 23, such that each of the phase affecting patterns is configured to affect light of different spectral range while substantially not affect propagation of light of other spectral ranges. The phase patterns 21-23, are configured as phase encoding for providing different amounts of extended depth of focus and focus shifts to the imaging lens unit. Such phase patterns or at least one of them may be configured for example using the technique disclosed in U.S. Pat. No. 7,365,917 assigned to the assignee of the present application. The phase patters are preferably configured to be non diffractive. This can be achieved by forming a phase patterns from a small number of phase affecting regions (i.e. low spatial frequency of the phase affecting regions), such that each of these regions has a dimension much larger than a wavelength, for example, much larger than 800 nm on either length or width of the region. The phase affecting pattern may be formed by one or more closed-loop phase affecting regions, e.g. a single ring-like region, or two or more spaced-apart concentric ring-like regions. Alternatively, the phase affecting pattern may be formed by one or more polygonal regions (e.g. rectangle); or by a grid (e.g. spaced-apart lines). Generally, the phase affecting region is a region on the surface of the lens region having a thickness different from that of its surroundings.

The different phase patterns are combined such that each of the patterns provides phase variations to a specific wavelength range only, while substantially not affecting light of different wavelength ranges. The wavelength ranges may be chosen to define the primary colors used for imaging, which are typically defined by Red (630-740 nm), Green (520-570 nm) and Blue (440-490 nm) colors.

As described above, the combined pattern 20 is configured to apply different phase encoding to light components of different colors (wavelength ranges). In this example, combined pattern 20 is a superposition of patterns 21, 22, and 23 configured for phase encoding of respectively light components at wavelength around 700 nm (red), light components at wavelength around 550 nm (green) and light components at wavelength around 470 nm (blue).

The combined phase coder pattern may be in a form of surface relief along the lens surface. Such surface relief provides that segments along the surface of the lens 10 are configured to be at different heights relative to the lens region and along the optical axis of the lens. These segments creating a height profile along the lens region induce variations to the optical path of light components passing through the lens region and therefore introduce phase variations to light output of the lens.

The combined phase pattern 20 can be described as a multi level profile such that every spectral range/wavelength of light passing through the multi level profile "experiences" a different phase profile. This is possible due to the cyclic nature of wave and the fact that the effective phase has periodicity of $2\pi$. The height profile of the lens surface preferably satisfies the following condition expressed by equation 1:

$$\delta d(x) = \frac{\lambda_R}{2\pi(n-1)}(2\pi N_R(x) + \varphi_d^{(R)}(x)) \qquad \text{(eqn. 1)}$$

$$= \frac{\lambda_G}{2\pi(n-1)}(2\pi N_G(x) + \varphi_d^{(G)}(x))$$

-continued $$= \frac{\lambda_B}{2\pi(n-1)}(2\pi N_B(x) + \varphi_d^{(B)}(x))$$

where $\delta d$ is the height profile along the surface of the lens; $\lambda_R$, $\lambda_G$, $\lambda_B$ are wavelengths for the red, green and blue spectral channels respectively; and $\phi_d^{(R)}(x)$, $\phi_d^{(G)}(x)$, $\phi_d^{(B)}(x)$ are the desired phage variations for the red, green and blue spectral channels respectively along the lens region (for example as shown is FIG. 2 by phase patterns 21, 22 and 23 respectively); $N_R(x)$, $N_G(x)$ and $N_B(x)$ are integer numbers which typically vary from the red, green and blue (or violet) channels respectively and also along positions on the lens region. It should be noted that both, the surface profile &i and the desired phase distribution/variation for each spectral channel ($\phi_d^{(R)}$, $\phi_d^{(G)}$, $\phi_d^{(B)}$), are functions of location x along the surface of the lens. In this specific example, the location x is described as a vector location along the surface of the lens.

The height profile described by equation 1 is configured to provide wavelength selective phase coding. Indeed, since the height differences are typically of the order of a few tens of wavelengths, the height differences may be of the order of a hundred wavelengths. Such large height variations provides flexibility in the phase variations by allowing selection of the integer numbers $N_R(x)$, $N_G(x)$ and $N_B(x)$ from a large range of numbers.

Equation 1 describes a height profile which is a result of combination/superposition of three different phase patterns, while each of these patterns effects a phase variation for the specific wavelength range (spectral channel) only. Since there is no exact analytical solution to equation 1, the design process may be done based on minimization of variations from equation 1, i.e. minimization of the mean square errors $\epsilon_R$, $\epsilon_G$ and $\epsilon_B$ for the three spectral channels. The minimization process allows calculation of the surface profile according to the following set of equation 2:

$$\varepsilon_R = \int \left| \frac{2\pi(n-1)}{\lambda_R} \delta d(x) - 2\pi N_R - \phi_d^{(R)}(x) \right|^2 dx \qquad \text{(eqn. 2)}$$

$$\varepsilon_G = \int \left| \frac{2\pi(n-1)}{\lambda_G} \delta d(x) - 2\pi N_G - \phi_d^{(G)}(x) \right|^2 dx$$

$$\varepsilon_B = \int \left| \frac{2\pi(n-1)}{\lambda_B} \delta d(x) - 2\pi N_B - \phi_d^{(B)}(x) \right|^2 dx$$

Such minimization of the errors provides for the solution for $N_R$, $N_G$ and $N_B$ and for the height, or surface, profile that will provide the desired phase pattern.

The phase patterns affecting the different spectral ranges are designed to provide for at least some of the spectral channels an extended depth of focus and/or focus shift.

Figure 3:
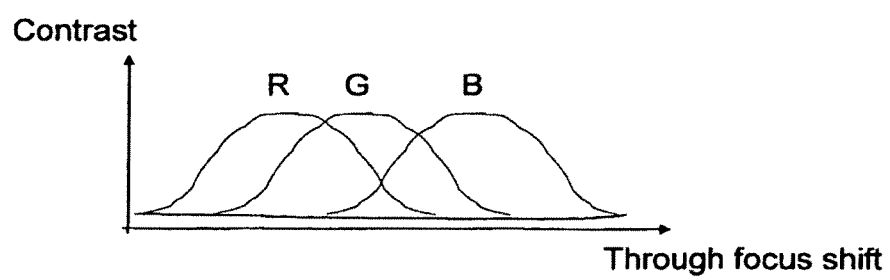
FIG. 3 shows an example of a through focus profile corresponding to polychromatic imaging achieved in the imaging lens unit of the invention.

Reference is made to FIG. 3 exemplifying the focusing effect of an imaging lens resulting from the above phase coding of the invention applied to the lens region, expressed in an imaging contrast for three spectral channels R, G and B, as a function of through focus shift (corresponding to the through focus MTF). It is clear from this figure that the imaging lens focuses different colors onto different focal planes with different depths of focus corresponding to a desired contrast pattern. The latter is such that the through focus MTF profiles for the different colors are preferably overlapping such as to form an envelope having an almost flat continuous region (or a plateau), around the original focal plane of the lens (i.e. with no phase coder). The phase coder is designed such that extended depth of focus achieved by the phase coder prevents or at least significantly reduces the contrast reduction.

The lens unit of the invention with the appropriate phase coder is characterized by extended depth of focus, as compared to that of the original lens, where the phase coder define a region along the optical axis of the lens and around or close to its original focal plane, where at any point along said region at least one color is represented by in-focus image while the other colors may or may not be in focus. Considering imaging applications, the brain adaptation process by a viewer can sharpen the information of the defocused channels to receive the visual spatial information through the focused channel and interpret the entire image accordingly. Such an imaging lens unit may be used for various imaging applications including inter alia ophthalmic applications such as spectacles, and ophthalmic lenses (contact lenses, intraocular lenses, intracorneal lenses, etc.).

The invention claimed is:

1. An imaging lens unit comprising:
    an imaging lens having a lens region and an effective aperture; and
    a phase coder located at the imaging lens, the phase coder comprising a surface relief formed by superposition of at least three phase patterns and comprising at least two elongated spaced-apart zones of a thickness different from that within a space between the zones, each phase pattern differently affecting light components of one of at least three different wavelength ranges while substantially not affecting propagation of light components of other of said at least three wavelength ranges, said surface relief affecting light propagation through the lens region to extend a depth of focus for at least one of said at least three wavelength ranges.

2. The imaging lens unit of claim 1, wherein said phase coder is integral with the imaging lens, said surface relief being that of at least one of surfaces of the lens within said lens region.

3. The imaging lens unit of claim 1, wherein said phase coder comprises at least one mask attached to at least one surface of the imaging lens within said lens region.

4. The imaging lens unit of claim 1, wherein said phase coder comprises a mask associated with a surface of the imaging lens within said lens region, said mask having one of the following configurations: (i) being integral with the lens region, (ii) being attached to the lens region, (iii) being spaced-apart from the lens region along an optical axis of the imaging lens.

5. The imaging lens unit of claim 1, wherein said surface relief is comprises a pattern having features arranged along said lens region, said features having predetermined dimensions along said lens region and along an optical axis of the imaging lens.

6. The imaging lens unit of claim 5, wherein said surface relief is configured to correspond to a predetermined height profile along the lens region, such that when polychromatic light passes through said lens region, a depth of focus for at least one of said at least three wavelength ranges in said light is extended.

7. The imaging lens unit of claim 6, wherein said predetermined height profile is such that when polychromatic light passes through said lens region, depths of focus for at least three wavelength ranges in said light are extended.

8. The imaging lens unit of claim 1, wherein said at least three wavelength ranges correspond to those of primary colors.

9. The imaging lens unit of claim 1, wherein the phase patterns comprise at least one closed-loop zone.

10. The imaging lens unit of claim 9, wherein said at least one closed-loop zone has a ring-like geometry.

11. The imaging lens unit of claim 9, wherein said at least one closed-loop zone has a polygonal geometry.

12. The imaging lens unit of claim 1, wherein the phase patterns comprise at least two spaced-apart zones.

13. The imaging lens unit of claim 1, configured for use in ophthalmic application.

14. The imaging lens unit of claim 13, configured for use as a contact lens.

15. The imaging lens unit of claim 13, configured for use as intraocular lens.

16. The imaging lens unit of claim 13, configured for use as spectacles lens.

17. The imaging lens unit of claim 13, configured for use as an intracorneal lens.

18. An imaging lens unit comprising:
    an imaging lens having a lens region and an effective aperture; and
    a phase coder located at the imaging lens, the phase coder comprising a surface relief formed by at least three phase patterns, wherein the phase patterns comprise at least one closed-loop zone having a polygonal geometry, each phase pattern differently affecting light components of one of at least three different wavelength ranges while substantially not affecting propagation of light components of other of said at least three wavelength ranges, said surface relief affecting light propagation through the lens region to extend a depth of focus for at least one of said at least three wavelength ranges.

19. The imaging lens unit of claim 18, wherein the phase patterns comprise at least two elongated-spaced-apart zones.

* * * * *